(12) United States Patent
Creighton, IV et al.

(10) Patent No.: US 6,311,082 B1
(45) Date of Patent: Oct. 30, 2001

(54) DIGITAL MAGNETIC SYSTEM FOR MAGNETIC SURGERY

(75) Inventors: Francis M. Creighton, IV, St. Louis; Bevil J. Hogg, Town & Country, both of MO (US); Rogers C. Ritter, Charlottesville, VA (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/251,164

(22) Filed: Feb. 17, 1999

Related U.S. Application Data (63) Continuation of application No. 09/189,725, filed on Nov. 10, 1998, now abandoned.
(60) Provisional application No. 60/065,104, filed on Nov. 11, 1997.

(51) Int. Cl.$^7$ ........................................... A61B 5/05
(52) U.S. Cl. .................................. 600/407; 600/415
(58) Field of Search .............................. 600/407, 410, 600/415, 420–425, 476; 324/318, 319, 322; 128/653.2, 653.5

(56) References Cited

U.S. PATENT DOCUMENTS

| | | | |
|---|---|---|---|
| 4,875,485 | * 10/1989 | Matsutani | 128/653 |
| 5,305,749 | * 4/1994 | Li et al. | 128/653.2 |
| 5,398,686 | * 3/1995 | Inoue et al. | 128/653.2 |
| 5,423,315 | * 6/1995 | Margosian et al. | 128/653.2 |
| 5,636,636 | * 6/1997 | Kuhn et al. | 128/653.2 |
| 5,654,864 | * 8/1997 | Ritter et al. | 361/141 |
| 5,931,781 | * 8/1999 | De Boer | 600/415 |
| 5,987,347 | * 11/1999 | Khoury et al. | 600/410 |

* cited by examiner

Primary Examiner—Tu Ba Hoang
(74) Attorney, Agent, or Firm—Harness Dickey & Pierce (57) ABSTRACT

A device and a method for guiding or applying force to a magnetic implant within the body of a patient. The device includes a bed for support of the patient, a set of separately energizable electromagnets or separately controllable permanent magnets so arranged to produce magnetic fields of varying orientations in a treatment region of the patient, and a processor that controls the currents in the electromagnets, or shutters on the permanent magnets to produce a selected magnetic field and/or gradient for guiding or moving the implant. The magnets are configured to allow a medical imaging device to be used to provide a real-time display of an operating procedure in which magnetic guidance is used. The method for guiding the implant includes the placing of the body on the bed, which may be servo-controlled, inserting a magnetically-guided implant into the treatment region, arranging the magnets around the body so that they can supply the necessary magnetic fields and/or gradients through appropriate energization of subsets of the magnets, and applying current or shutter control to subsets of the magnets to provide a guiding magnetic field for the implant, which may occur while real-time medical imaging of the procedure is occurring. The bed may be moved under servo control to provide further control of the direction and magnitude of the magnetic field affecting the implant.

18 Claims, 6 Drawing Sheets

DIGITAL MAGNETIC SYSTEM FOR MAGNETIC SURGERY

CROSS-REFERENCE TO RELATED APPLICATION

This application is a continuation of prior U.S. patent application Ser. No. 09/189,725, filed Nov. 10, 1998, now abandoned, and of prior provisional U.S. patent application Ser. No. 60/065,104, filed Nov. 11, 1997.

BACKGROUND OF THE INVENTION

1. Field of the Invention

This invention relates to the field of surgery, and more specifically to a device and method for guiding or applying force to a magnetic implant within the body of a patient.

2. Description of Related Art

It is known in the art to provide magnetic manipulation of diagnostic or therapeutic elements (which, for simplicity, we shall herein refer to collectively as "treatment implants") through body tissue or ducts (such as in vascular exploration or treatment). Systems providing for such manipulation are described in a number of previously published articles and patents, such as "Magnetically Guided Devices for Vascular Exploration and Treatment," Sadek K. Hilal et al., Radiology 113, 529–540 (1974); U.S. Pat. No. 3,358,676, entitled "Magnetic Propulsion of Diagnostic or Therapeutic Elements Through the Body Ducts of Animals or Human Patients," issued Dec. 19, 1967 to Ephraim H. Frei et al.; "Magnetic Manipulation Instrumentation for Medical Physics Research," George T. Gillies et al., Review of Scientific Instruments 65, 533–562 (1994); "Characteristics of an Improved Magnetic-Implant Guidance System," Robert G. McNeil et al., IEEE Trans. on Bio. Eng. 42(8) 802–808 (1995); "Functional Design Features and Initial Performance Characteristics of a Magnetic-Implant Guidance System for Stereotactic Neurosurgery," Robert G. McNeil et al., IEEE Trans. on Bio. Eng. 42(8) 793–801 (1995); and U.S. Pat. No. 5,654,864 to Ritter et al., entitled "Control Method for Magnetic Stereotaxis System," issued Aug. 5, 1997. All of these references are hereby incorporated in their entirety by reference. These systems all provide fixed or manually moved permanent magnets or electromagnets that are capable of applying fields and forces to treatment implants to move or guide the implant through a treatment region. However, because the magnets or electromagnets for these systems are large, it is difficult or impossible to provide complex imaging systems that can operate in conjunction with the magnetic guidance system. In addition, because of the limited ability to move the magnets or electromagnets, it is difficult to apply fields and forces accurately directed at accurately known locations.

SUMMARY OF THE INVENTION

It is thus an object of the invention to provide a magnetic system for guiding the movement of a treatment implant in a treatment region of a body.

It is a further object of the invention to provide a magnetic guidance or propulsion system that permits complex and useful imaging systems to be used during magnetic guidance operation.

It is yet a further object of the invention to provide a magnetic guidance or propulsion system that permits complex and useful imaging systems to be used stereotactically and in an efficient manner during magnetic guidance operation.

It is yet another object of the invention to provide a method for performing magnetic guidance or propulsion of a treatment implant while simultaneously allowing complex and useful imaging systems to be used to help direct the guidance or propulsion of the treatment implant.

There is thus provided, according to a first aspect of the invention, an apparatus for producing a magnetic field to control a trajectory of a treatment implant in a treatment region of a body comprising: a bed configured to support a patient; a plurality of separately energizable electromagnets configured to produce magnetic fields of varying orientations in a treatment region of a patient supported by the bed; and a processor configured to control currents in subsets of the plurality of separately energizable electromagnets to generate a magnetic field having at least approximately a selected orientation and field strength. The bed may be moveable and controlled by a servo-system to aid in applying an accurately controlled magnetic field in the region of the treatment implant. In addition, one or more fluoroscopic or other medical imaging devices (which may or may not be fixed) may be provided, the illumination apparatus for which may be directed between gaps in the plurality of the coils, to provide a useful, effective, and possibly stereotactic display for a surgeon directing the surgery of the patient.

In another embodiment of the invention, the invention comprises an apparatus for producing a magnetic field to control a trajectory of a treatment implant in a treatment region of a body comprising: (a) a moveable bed configured to support a patient; (b) at least one medical imaging screen and medical imaging illuminator, which may or may not be fixed system, configured to provide a medical image of a patient supported by the moveable bed; (c) a set of electromagnets under the moveable bed, each configured to provide a magnetic field having different orientations in a treatment region of a patient supported by the moveable bed; (d) a servo control configured to move at least one of the bed or the set of electromagnets; and (e) a power source configured to selectively provide a selected amount of current to a subset of the set of electromagnets, the amount of current and the subset of the set of electromagnets being a function of time.

In yet another embodiment of the invention, the invention comprises a method for guiding an implant through a treatment region of a body comprising the steps of: (a) placing a body on a servo-controlled, moveable bed; (b) inserting a magnetically-guided treatment implant into the treatment region; (c) arranging a plurality of electromagnets around the treatment region so that a selected orientation of a magnetic at a location of the treatment implant can be approximated by selectively energizing a subset of the electromagnets, moving the bed, or both, as the case may be; (d) applying current to a selected subset of the plurality of electromagnets to provide a magnetic field at least approximating a selected magnitude and orientation at the location of the magnetically-guided treatment implant. During the applying step, medical imaging of the treatment region may be provided.

In one embodiment of the invention, a servo-controlled bed is provided for a patient. Preferably, but not necessarily, the bed is arranged for the patient to lie supine. One, or more preferably two or more fluoroscopes or other medical imaging devices are provided having screens above the supine body of the patient. A part of the body, which shall be referred to herein as the "treatment region," is to be placed below the screens of the fluoroscopes. An array of electromagnets, which may, but need not be superconducting, is provided and configured to provide, when one or more electromagnets are energized, an effective magnetic field in the treatment region of the body when the treatment region is below the screens of the fluoroscopes.

To place the treatment region of the body into the necessary position below the fluoroscopes, a computer or other servomechanism controls motion of the bed carrying the patient. Alternately, both the bed carrying the patient and the electromagnets may be moved. In an alternate embodiment of the invention, the bed and/or the electromagnets may be configured for manual movement as needed, if servo control is not provided for initial position of the patient, or as an optional alternative to servo control when it is provided.

In still another embodiment of the invention the electromagnets are replaced by permanent magnets, which may either be moved back and forth along their axes in order to change the overall field at the operating point in a patient, or they may employ shutter-like or keeper-like permeable material to organize the contributions of the individual magnets to the field at a particular location in a patient.

DESCRIPTION OF THE PREFERRED EMBODIMENTS

For convenience, a fluoroscopic system is described in the detailed description below. However, other similar forms of medical imaging and medical imaging devices may generally be substituted, which may or may not be fixed relative to the patient or the electromagnets described herein. It should also be understood that the use of the term "guiding" is not meant to exclude cases in which a pulling or pushing force as well as guiding force is applied.

Figure 1:
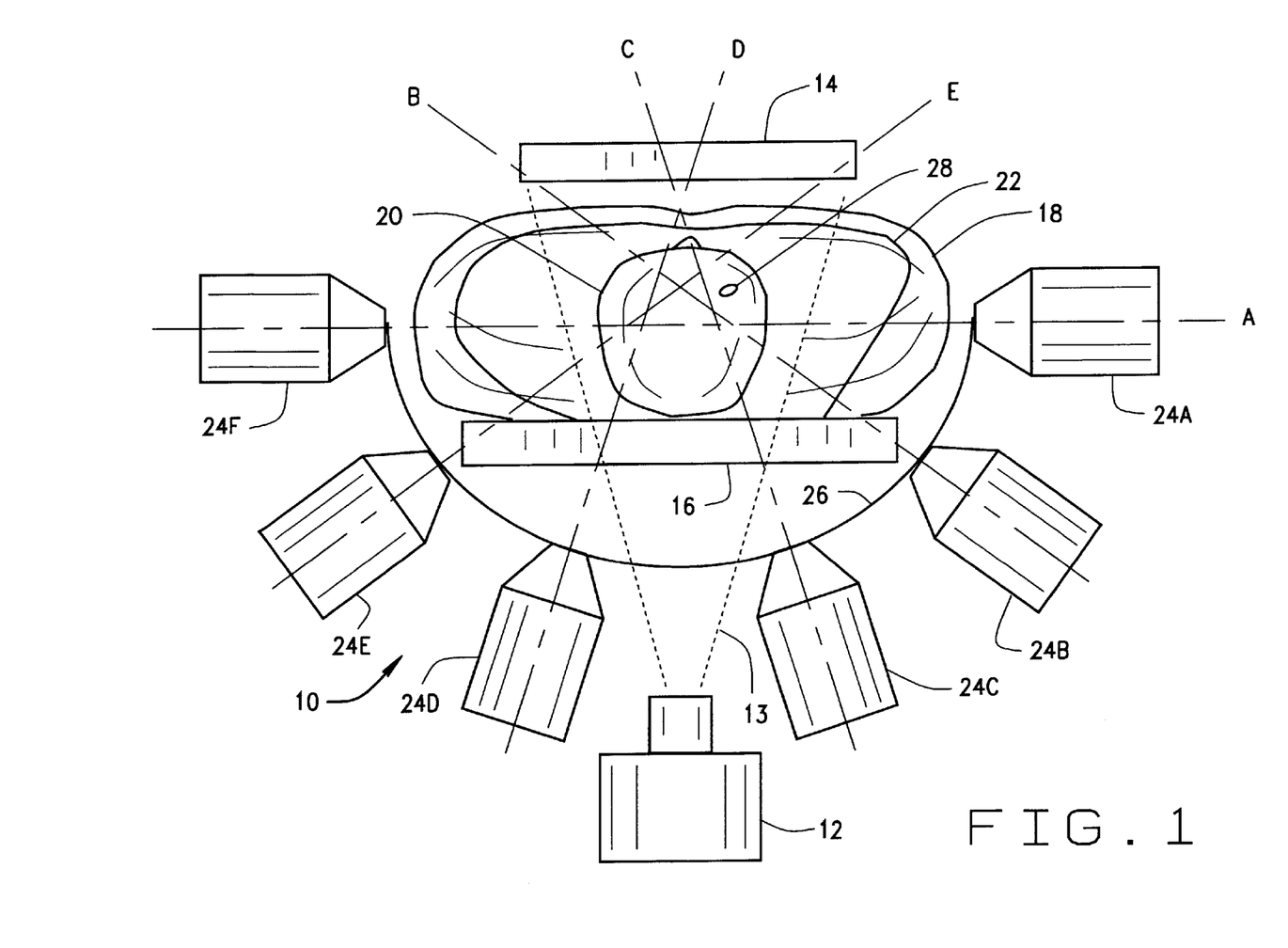
FIG. 1 is a partial sectional view of an embodiment of a digital magnetic system for magnetic surgery in accordance with the invention.

An apparatus 10 in accordance with the invention is partially represented in FIG. 1. The inventive apparatus 10 comprises, in part, a fluoroscope illumination device 12 which projects a beam 13 towards fluoroscope screen 14. A moveable bed 16 is disposed between fluoroscope illumination device 12 and fluoroscope screen 14. A patient 18 (represented schematically with head 20, oriented with his longitudinal axis extending in a direction out of the page) is shown in a supine position on bed 16. Beam 13 is thus projected through a treatment region 22 in the body of patient 18 so that a fluoroscopic view of this region appears on screen 14. For purposes of illustration, and without loss of generality, the treatment region 22 shall be assumed to be located in the patient's midsection, although this will vary according to the surgical procedure being performed. It will be apparent to those skilled in the art that the apparatus could be described with respect to a treatment region 22 elsewhere in the body.

In a typical configuration of the inventive apparatus, the surface of the bed 16 is rectangular and has a shorter and a longer dimension. The longer dimension would be sufficient to accommodate the length of a patient's body from head to toe. Typically, the patient will be lying on the bed in this orientation when the inventive apparatus is used to create a reference axis in the caudal-cranial direction. It should be understood, however, that an orientation of the patient or bed shape other than that described herein may be dictated by surgical requirements.

A moving apparatus (not shown in FIG. 1) controlled by a computer or other servomechanism, (also not shown in FIG. 1) is provided so that bed 16 is moveable along at least a longitudinal axis and preferably also a transverse axis. The servo-controlled bed is controlled to place the treatment region between the fluoroscope illumination device 12 (or devices 12, if more than one is provided) and the fluoroscope screen 14 (or screens 14, if more than one is provided for multiple views of the treatment region). An array of electromagnets (six of which, 24A–24F, are shown in FIG. 1) is provided. Rows of electromagnets represented by electromagnets 24A–24F are provided in sufficient number and in orientations so that, by energizing an appropriate subset of the electromagnets, a magnetic field in any orientation can be provided, at least approximately, in the treatment region of the body. The electromagnets 24A–24F preferably are juxtaposed so that a field of at least 0.10 Tesla and more preferably 0.3 Tesla can be provided at any point within and to or from the regions of the abdominal cavity, chest cavity, head and arteries of a patient, depending upon the position of the bed, the translation (if any) applied to the electromagnets, and the selection of and current applied to the electromagnets. The electromagnets may be normally conducting (i.e., resistive wire electromagnets) or superconducting, the latter preferably comprising high-temperature superconductors. The electromagnets are arrayed with at least one gap arranged so that the electromagnets do not obstruct the medical imaging apparatus 13, 14.

In the cross-sectional view of FIG. 1 (which also shows, for orientation purposes, the head 20 of patient 18) only one electromagnet 24A–24F is shown from each row. Other electromagnets, not shown, would be mounted above and below the plane of FIG. 1. These electromagnets are mounted on or affixed to a curved shell 26 which surrounds one-half (or approximately one-half) of the treatment region from below. Shell 26 is curved, not only within the range shown in the cross-section of FIG. 1, but also in the directions into and out of the page, so that the other electromagnets in the different rows to which electromagnets 24A–24F belong are also directed towards the treatment region, but along axes that cross the treatment region 22 at various angles. Thus, while electromagnets 24A–24F provide magnetic fields in the treatment region essentially along axes A–E in the same plane as FIG. 1, the other electromagnets, not shown, provide magnetic fields oriented in directions other than parallel with the planar section of treatment region 22 drawn in FIG. 1.

It should be recognized that, although the mounting means for electromagnets 24 (and 24A–24F, which should be considered for purposes of discussion as being included when electromagnets 24 are referred to) is described as a shell, it is not necessary that an actual shell be used. Any suitable means for supporting the array electromagnets in a similar arrangement, preferably one that includes at least one gap between the electromagnets large enough to pass radiation from a medical imaging illuminator, may be used.

Electromagnets 24A–24F (and others not shown) are arrayed to have their individual axes in appropriate directions to provide, through the energizing of appropriate subsets of the electromagnets, a magnetic field needed at any place in the treatment region, directed in any needed direction. In the embodiment shown in FIG. 1, magnets 24A–24F (and others not shown) are oriented to provide an array of forces that cover half of the treatment region from below. By reversing currents, the magnetic fields can be made to provide the opposite direction of guidance, for acting on a cylindrical permanent magnet implant. That is, the magnetic field B of each coil can be reversed as needed. A magnetic implant 28 (either a permanent magnet or an induced magnet of permeable material) inside the treatment region of the body is guided by the electromagnets 24. It is envisioned that magnetic implant 28 is a seed for delivering therapy to a particular portion of the body of patient 18, although it could also represent a magnetic catheter tip or other device that can be magnetically guided through the body. In operation, patient 18 is supine on servo-controlled bed 16, which is controlled by a computer or other servo-control element to place that portion of a body that is of interest at any given time during the medical procedure being performed below the screen 14 of a fluoroscope (or below the screen 14 of one of two or more fluoroscopes) to provide real-time imaging. Bed 16 may also, or alternately, be manually moveable for this purpose. The treatment region, at any particular time, includes seed 28.

Figure 2:
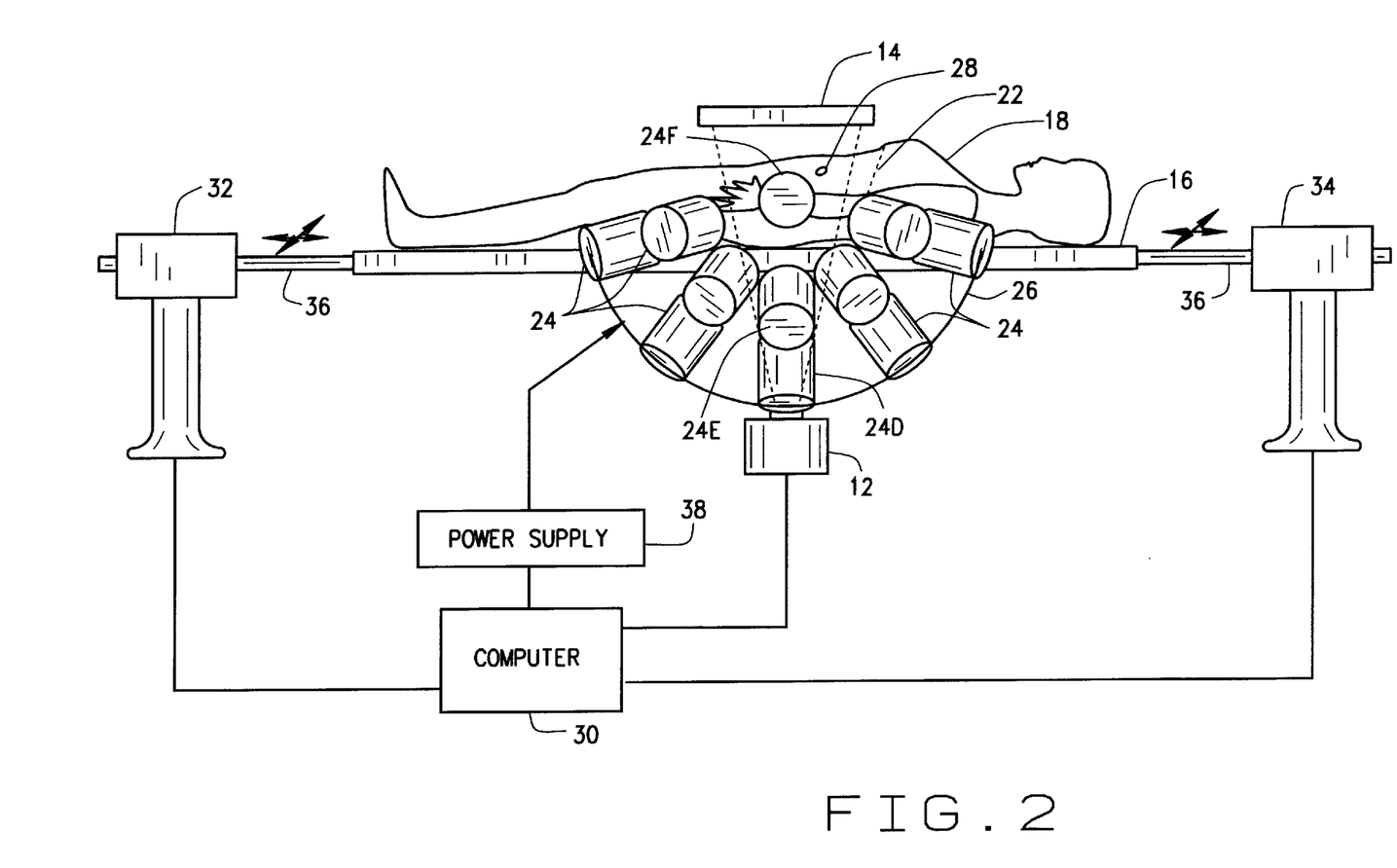
FIG. 2 is a side view of the embodiment of FIG. 1.

FIG. 2 shows, in schematic form, a side view of the apparatus shown in FIG. 1. Electromagnets 24 are shown in a plurality of rows, and include electromagnets 24D, 24E, and 24F which are also shown in FIG. 1. One or more electromagnets 24 may be energized as necessary to provide a needed guiding field or force at each location where needed to guide magnetic seed 28 as it moves through the body. The magnetic fields from each energized coil add as a vector sum, and since a plurality of coils with orientations in different directions are provided, only one or a few coils actually need to be energized to produce any required magnetic field orientation and magnitude. A computer 30, which may be the same as the computer that guides the movement of bed 16 (if the bed is not moved manually) may be used to control the application of power to the electromagnets 24 as well as fluoroscope illuminator 12. A field produced in a treatment region of body 18 can be modulated by progressive activation of the subsets of the electromagnets as needed to guide or move implant 28 and/or gradual change in the currents through the energized electromagnets. (This progressive changing of subsets of energized electromagnets and gradual changing of the currents in the energized electromagnets shall be referred to as a "wavelike" change, because it is gradual, "propagates" through nearby coils in a specific direction [as determined by surgical requirements], and, for periods of time, is either continuous in time or approximately so. It should be understood that this term is not being used to refer to electromagnetic radiation as such.)

As the implant or seed 28 moves, the amount of current in the activated one or ones of coils 24 will change, usually with adjacent coils to the set also being gradually energized or de-energized, so that the activation itself can be considered as smoothly travelling through the set of coils 24. To keep the treatment region within the range within which the needed magnetic field can be accurately produced in magnitude and orientation with the number of electromagnetic coils 24 provided, bed 16, shell 26, or both can be moved through a servomechanism as the seed 28 moves. This action may be controlled by computer 30. An example of a servo system is shown in FIG. 2 as follows. Bed 16 is supported by stands 32, 34. Stand 34 contains a servomechanism (not shown) that controls either longitudinal or transverse motion of rods 36 which carry bed 16. Stand 32 contains a coupling mechanism that allows rods 36 to move so that the servomechanism can smoothly move bed 16 relative to shell 26. This example of a servo system is provided only as an example, as one skilled in the art would be able to provide numerous other suitable configurations.

Current is supplied to electromagnets 24 by a power supply 38, which may actually comprise a plurality of power supplies for independently supplying individual currents to the various magnets. Power supply 38 is (or the actual independent power supplies are) controlled by computer 30. Current in each energized coil 24 may be reversed as needed, if the direction of the magnetic field must be reversed. Optionally, medical imaging device 12 may also be controlled by computer 30.

Figure 3A:
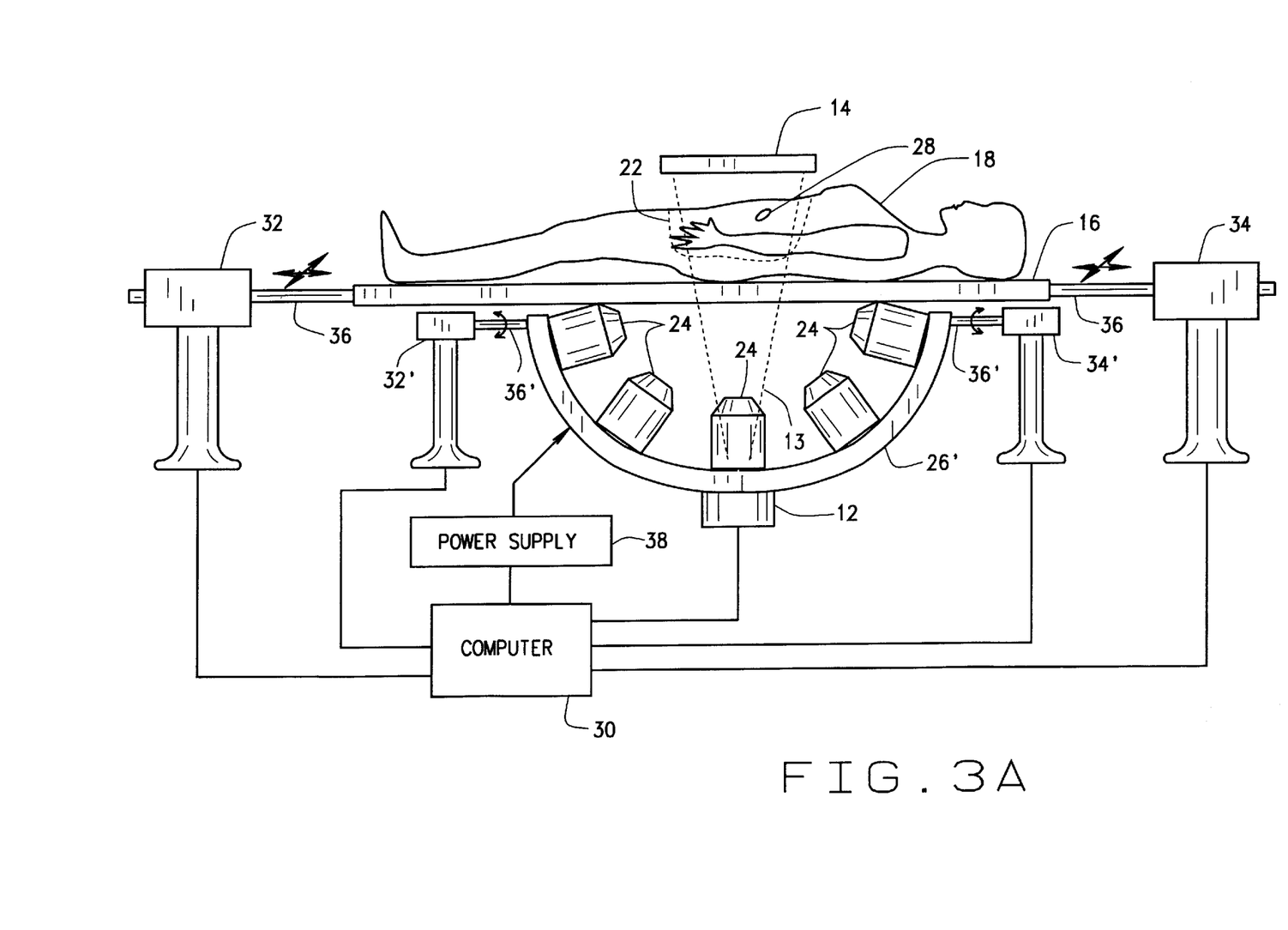
FIG. 3A is a side view of another embodiment of a digital magnetic system for magnetic surgery in accordance with the invention.

In an alternate embodiment shown schematically in FIG. 3A, a single row of electromagnetic coils 24 is provided. This single row may be translated or rotated so as to cover, in a manner similar to that of the array shown in FIG. 2, the application of the magnetic fields to the treatment region (i.e., the operating region). In the particular embodiment illustrated in FIG. 3A, an elongate, arcuate support 26' on which magnets 24 are mounted is preferably rotatable in such a fashion that its surface traces out a curve similar to the shape of shell 26 in FIG. 2, so that the electromagnets 24 thereon can be energized in any position to provide the needed magnitude and direction of magnetic field in the treatment region of the body. This rotation can be accomplished by pivoting arcuate support 26' under servo control. By way of example only, this pivoting mechanism as illustrated includes rods 36' that are fixedly attached to arcuate support 26' at each end and that rotate within supports 32' and 34'. Support 34' includes a motor (not shown) that is responsive to computer 30 for rotating rod 36' within support 34'. Alternately, with an appropriate, but different, supporting structure, arcuate support member 26' could be pivoted on a vertical axis, and rotated out of the plane of FIG. 3A. Various modifications of this embodiment are possible. For example, any moveable supporting means may be provided, and alternate structures for providing pivoting or rotational movement of the supporting means may be provided.

Figure 3B:
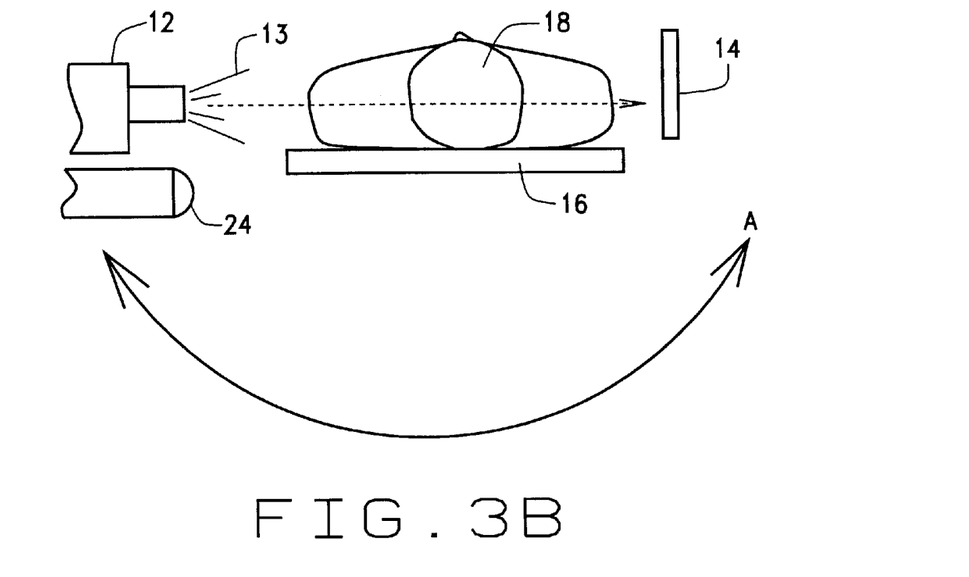
FIG. 3B is a view of a portion of the apparatus of FIG. 3A from a point along the longitudinal axis of a patient.

FIG. 3B provides another view of a portion of the embodiment of the apparatus shown in FIG. 3A. The view in FIG. 3B is from a point on a longitudinal axis of patient 18 above the head. Only one magnet 24 is shown, which, in FIG. 3B, is shown in a position essentially all the way to one side of patient 18 rather than directly below the patient, as in FIG. 3A. The direction of rotation of support 26' is indicated by arrow A, although support 26' is not itself shown in FIG. 3B. FIG. 3B also illustrates that fluoroscopic illuminating device 12 may be physically coupled to support 26' so that it travels with the support arm, in which case either a plurality of imaging devices 14 would have to be provided to intercept beam 13 at the various possible orientations of support 26', or imaging device 14 could be mechanically or otherwise coupled to support 26' so that it remains within beam 13 from illuminating device 12 as illuminating device 12 moves from position to position along with magnets 24. Illuminating device 12 may also be disposed in a fixed position, such as beneath bed 16 as shown in FIG. 3A. In this case, rather than being supported by support 26' as suggested by FIG. 3A, the illuminating device 12 would preferably be disposed below the lowest point of the swing of support 26' so that illuminating device 12 does not interfere with the motion of support 26'.

In those cases in which the electromagnets must provide a gradient to produce not just guidance, but also a pulling or pushing force on an implant, an array similar to that shown in FIG. 2 (or FIG. 3A) is needed above the patient 18, since it not possible to push a free permanent magnet away from a source. (If free, the magnet will flip to reverse its ends so as to align itself with the field, because a permanent magnet anti-aligned with a field, i.e., in the pushing direction, is critically stable and will tend away from the critically stable direction if not constrained.) Thus, all directions of pull must be provided if force is to be applied by the electromagnets.

Alternately, the second array, or each of the two arrays, can comprise a single row that is translated and/or rotated about the patient to accomplish the same coverage of pulling directions. Such translation or rotation may require an array to be positionable at one side of or above bed 16, as well as being positionable under bed 16.

There is a "granularity" in the field directions that can be applied by an arrangement of finite electromagnetic sources each in a different location and pointing in a different direction. Consequently, the computer controlling the currents in the electromagnets may calculate the combination of currents of a small cluster of the magnets in order to provide a field in any direction. Such a calculation would not be necessary when the required field is closely along the axis of one of the electromagnets, or if minor directional errors are tolerable, such as for motion within vessels. Movement of the patient bed is an additional way of providing flexibility of the available field directions. Individual electromagnets 24 (or as represented by 24A–24F) may also be made pivotable in unison about a common axis or their individual axes.

Figure 4:
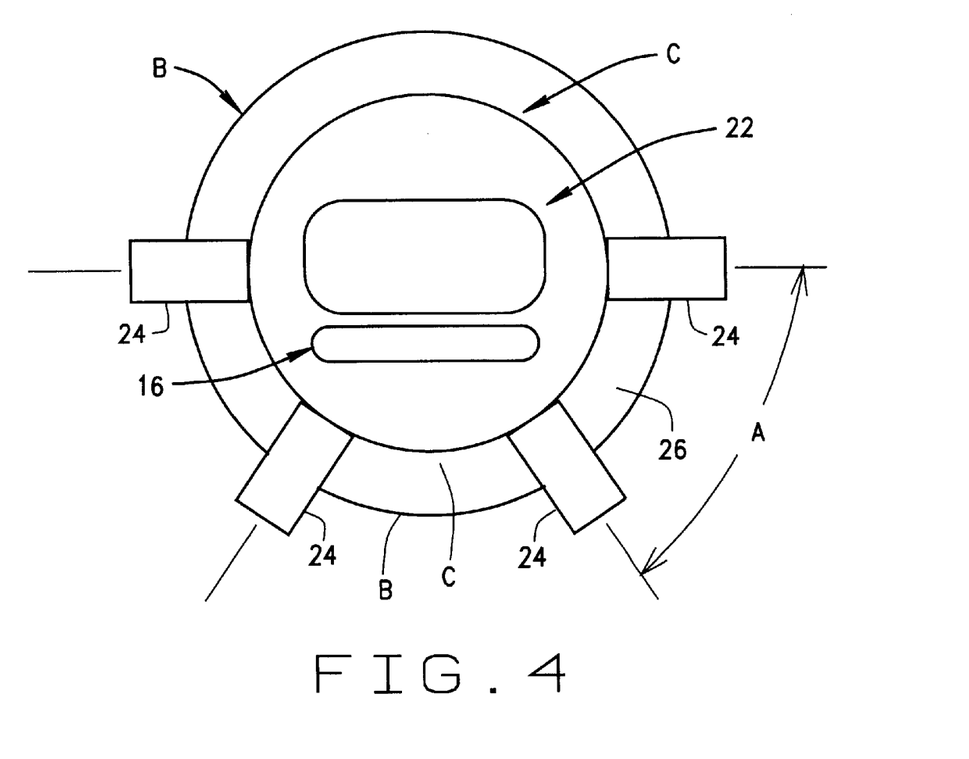
FIG. 4 is a partial transverse cross sectional view of a typical embodiment of the invention employing superconducting coils.
Figure 5:
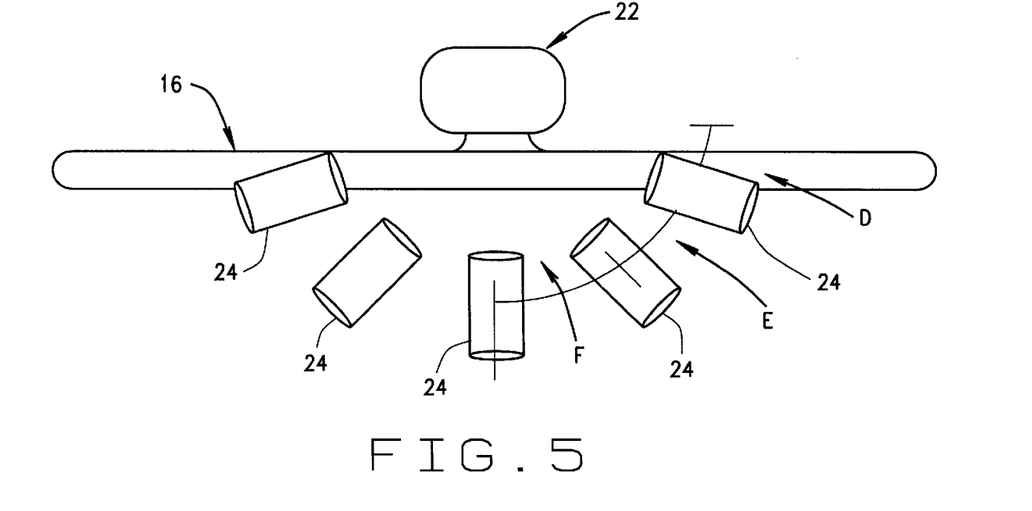
FIG. 5 is a partial longitudinal cross sectional view of the embodiment of FIG. 4.

FIG. 4 shows a transverse cross-section of a portion of a typical embodiment of the invention employing a twenty coil, whole body coil arrangement of superconducting magnets 24. Because the magnets are superconducting, only twenty are typically required, four of which are shown in FIG. 4. (If non-superconducting coils are used, as a general rule, about twice as many would be required.) The magnets 24 are mounted on circular shell 26 having an outside diameter B of 29 inches, and an inside diameter C of 22 inches. This arrangement is sufficient to accommodate a treatment region having a 7" by 15" cross section, as shown. The angle A between adjacent coils in this side view is 60 degrees. FIG. 5 shows a longitudinal partial cross section of the apparatus of FIG. 4, showing the planes of the five rows of coils (for clarity, not all coils are shown). The angle D indicated in FIG. 5 between the axis of a coil closest a plane parallel to bed 16 and that plane is 15 degrees. The angles F and F between the adjacent rows of coils is 37.5 degrees.

Many further modifications of the inventive apparatuses so far described are possible. For example, electromagnets 24 may be placed closer to the body to enable procedures at locations difficult to reach without more powerful magnets. To position electromagnets 24 closer to the body, their positions may be made adjustable along their respective axes. Fluoroscopic imaging may be replaced by 3-dimensional ultrasound, which might be adjusted more optimally for the adjustable electromagnets. In an extreme case, electromagnets 24 could be part of a "pelvic girdle" pushed right against a patient's body. Thin ultrasonic probes could be squeezed between the magnets to provide the necessary contact with the patient's skin. Guidance of a magnetically tipped endoscope with such a system via the optical channel of the endoscope supports the simpler visualization of the ultrasound, as compared with precision bi-plane fluoroscopy.

There are numerous applications for the inventive apparatus, which may be used for magnetic field guidance, magnetic field control, magnetic force application, and combined guidance and force application. Different computer software may be necessary to accomplish these or other intended purposes, as is known to those of ordinary skill in the art.

Operating as a magnetic field guidance device, a practical coil array and its controllers will apply an accurately directed uniform magnetic field of a prescribed magnitude over a region of a few centimeters in diameter. The field will apply a torque on a magnetic implant to align it in the required direction, namely along the direction of the magnetic field.

When operated as a magnetic control device, a system will apply an accurately directed and uniform magnetic field over one or more regions at a given time to provide some control over an implant in that region. One such use of the inventive system is the stiffening of otherwise flexible permeable guide wires that are pushing an endoscope, catheter, or other therapeutic device, when the trajectory is such that the wire would tend to bow in an undesired loop.

When operated as a magnetic force applicator, a system in accordance with the invention would provide a uniform gradient over a small region, at times one or two centimeters in diameter, which can act on a permanent magnet implant to provide a translational force on that implant in a desired direction.

When operating as a combined guidance and force applicator, a system in accordance with the invention will provide the most feasible approximation to having a combination of both a transversely uniform orienting field and a longitudinal field gradient to both torque and pull in an implant in a desired direction.

A surgeon operating a system in accordance with the invention may, with the aid of the imaging provided by fluoroscope screen or screens 14, provide the guiding direction to a computer through an input such as a joy-stick. The computer then would calculate the currents required to provide the guiding field at the location of the implant. Then, as the implant proceeds along a path, the surgeon would provide new directions as needed. The bed position is changed smoothly by the computer to keep the implant in the imaging treatment region, or to provide more accurately directed and stronger magnetic fields if required. The fluoroscope or other medical imaging system may be used to freely view the region of approach and procedure. The fluoroscope may be used by the surgeon preoperatively or in real time, and may be stereotactically connectable to the magnet system.

In use, the patient would be placed on the bed and a magnetically-guided treatment implant would be implanted in the treatment region. The treatment implant may be any one of numerous types of implants. By way of example only, and without the intention of limiting the types of implants that may be used, the treatment implant may be an endoscope with an attached magnetic implant, an endoscope with a magnetic implant contained within the endoscope, a catheter with a magnetic implant contained within or attached to it, an catheter or an endoscope with one or more magnetic sections that are to be stiffened by the applied magnetic field, or the like. Also by way of example only, the magnetic field may be used to manipulate the direction of a leading edge of a catheter or endoscope.

The electromagnets of the device are then arranged around the patient (such as by moving the bed with the patient on it into the apparatus) so that the treatment region including the treatment implant is at a location in which a magnetic field of an orientation and magnitude selected by the surgeon can be approximated by selectively energizing a subset of the electromagnets, moving the bed, or both, as required. Current is then applied to the electromagnets to approximate this field. The medical display in the apparatus may be activated during this time to provide a real-time display of the procedure by directing the medical imaging illuminator through a gap in the arrangement of the electromagnets, through the treatment region, and towards an imaging screen. The currents in the electromagnets, and the electromagnets that are energized may be changed continuously to provide a time-varying magnetic field to guide the treatment implant. Also, the location of the electromagnets and the location of the bed may be moved either individually or in combination, as provided by the apparatus, under servo-control or manually, to more accurately produce the required fields in the treatment region as the treatment implant is moved.

In another embodiment of the invention that employs permanent magnets, the general arrangement of magnets near a patient may be similar, but with intervening permeable shutter material, or alternately, with solenoids moving the individual magnets to provide the equivalent of the above described "wavelike motion" of the field.

Figure 6:
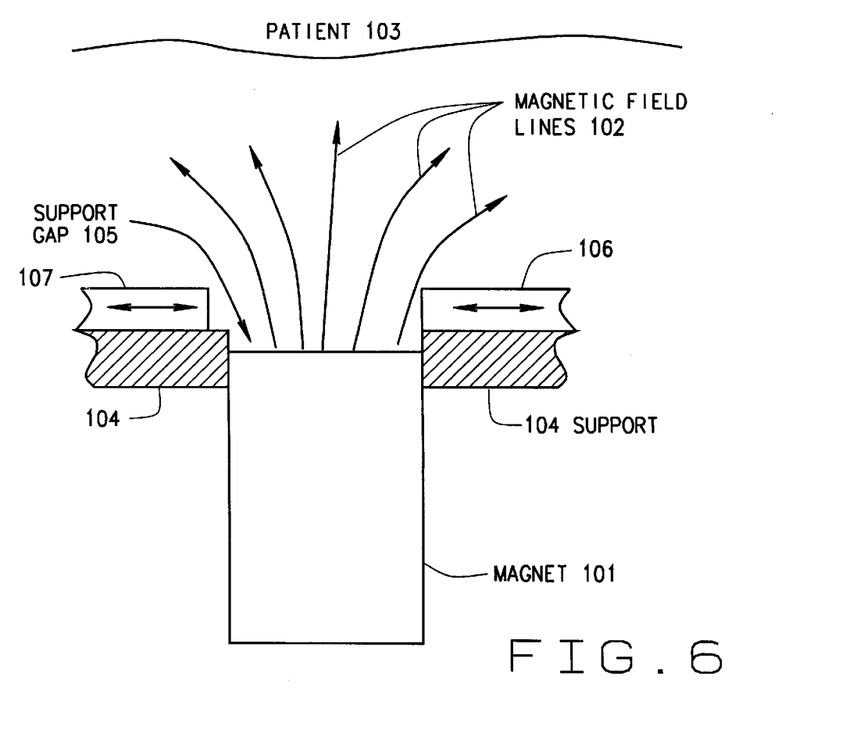
FIG. 6 is a diagram of a shutter mechanism for an individual permanent magnet to provide control of the degree of its magnetic field that reaches a point in a patient.

FIG. 6 shows the operation of shutters on a single magnet 101, which projects field lines 102 in the direction of patient 103 (not shown to scale). Magnet 101 is firmly mounted to non-magnetic support frame 104, which has gap 105. Sliding magnetically permeable sections 106, 107, can move over the front of gap 105 by varying amounts to control projection of magnetic field lines 102, by providing favorable flux path to rear of magnet, shown in FIGS. 7A and 7B.

Figure 7A:
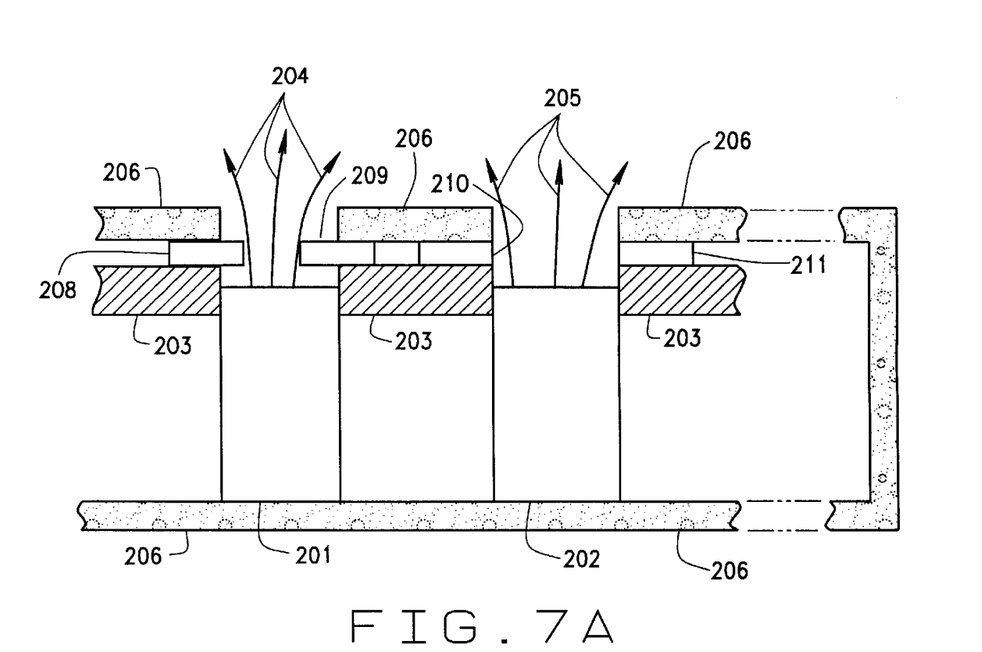
FIGS. 7A and 7B are diagrams showing how a shutter mechanism can work with two adjacent permanent magnets to provide control over the way they contribute to the field at a location in a patient, with FIG. 7A being a side view and FIG. 7B being a top view.
Figure 7B:
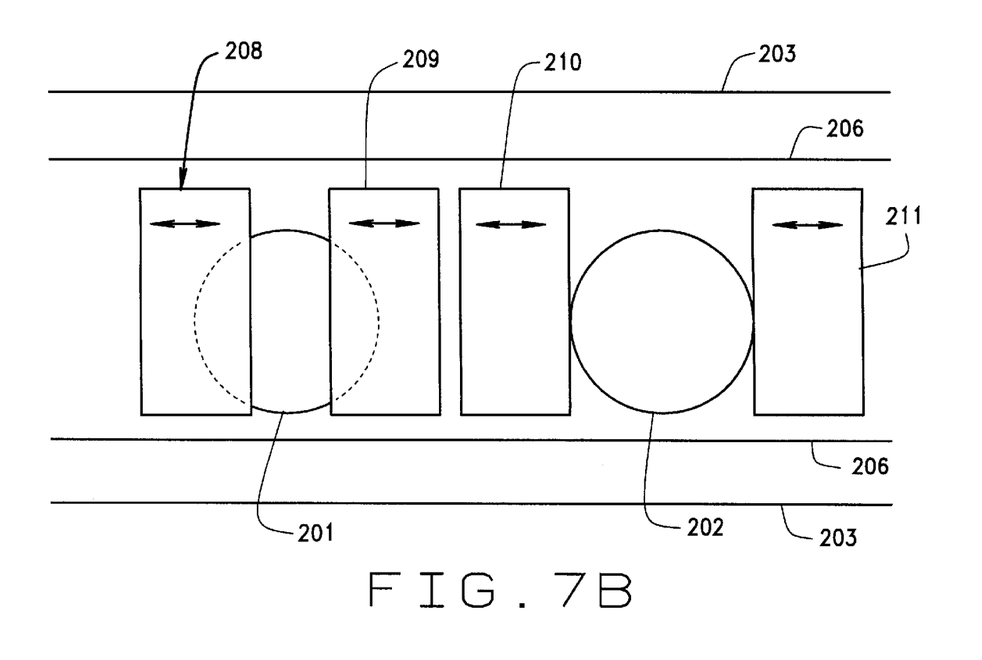

FIG. 7A is a side view showing the operation of shutters and flux return path on two adjacent magnets 201 and 202 mounted to nonmagnetic support 203. Field lines 204 and 205 emanate from magnets 201 and 202, respectively. Fixed magnetically permeable lattice and return path 206 has gap in front of each magnet, shown also in Top view 7B. Independently sliding magnetically permeable shutters 208, 209, 210 and 211 can by varying degrees cover all or part of one half of each circular gap in support 203 and in fixed permeable lattice 206, as needed to control magnitude and direction (somewhat) of projected magnetic field, a combination of 204 and 205, towards patient. Fixed permeable lattice 206 securely contacts magnets 201 and 202 at rear, providing a return flux path much more favorable than air, so as to guide magnetic field lines controllably away from a patient in desired amounts.

FIG. 7B is a top view showing sliding shutters 208, 209, 210 and 211 covering part of gap for magnet 201 and none of gap for magnet 202, in support 203 and lattice 206.

It should be noted that the sliding shutter widths and distances between magnets should be such as to allow full motion of all of the shutters.

Motions of sliding shutters 208, 209, 210 and 211 are independent, and could be derived from rack and pinion gears driven by magnetic field immune servomotors. Sliding elements should move smoothly, and should be mounted in tracks, preferably with Teflon films to reduce friction.

It will be noted that in the embodiment shown in FIGS. 6, 7A and 7B that there is no provision for reversing the direction of magnetic field from the permanent magnet. In this embodiment the system should either be moveable around the axis of the patient's body, or two or more such arrays should be provided. The "reach" of the magnet assembly from any one side of a patient in such a case should be completely across the procedure region in the patient, unlike the case for electromagnets.

It can be seen by one skilled in magnetic circuitry and in mechanical devices, that there are many other mechanisms, which will accomplish the same or similar effects on adjusting magnetic fields projected towards a patient. It will also be recognized that the inventive apparatuses, together with the inventive methods disclosed herein, have an advantage over manually moved permanent magnets or electromagnets in that fields and forces can be applied that are accurately directed at accurately-known locations. Also provided is an advantage over the magnetic stereotaxis system and other magnetic guidance and propulsion systems in the inventive systems are much more flexible in their applications, permitting more complex and useful imaging systems to be used, in some applications stereotactically in a more effective manner.

One skilled in the art would recognize that many modifications are possible within the spirit of the invention. Therefore, the scope of the invention is not to be limited solely to the exemplary embodiments described above, but should be determined with reference to the claims appended below, together with the full scope of equivalents permitted under applicable law.

What is claimed is:

1. An apparatus for producing a magnetic field to control a trajectory of a treatment implant in a treatment region of a body comprising:

(a) a moveable bed configured to support a patient;

(b) at least one medical imaging screen and medical imaging illuminator configured to provide a medical image of a patient supported by the moveable bed;

(c) a set of electromagnets under the moveable bed, each configured to provide a magnetic field having different orientations in a treatment region of a patient supported by the moveable bed;

(d) a servo control configured to move at least one of the bed or the set of electromagnets; and (e) a power source configured to selectively provide a selected amount of current to a subset of the set of electromagnets, the amount of current and the subset of the set of electromagnets being a function of time.

2. An apparatus for producing a magnetic field to control a trajectory of a treatment implant in a treatment region of a body comprising:

a bed configured to support a patient;

a plurality of separately energizable electromagnets configured to produce magnetic fields of varying orientations in a treatment region of a patient supported by the bed; and a processor configured to control currents in subsets of the plurality of separately energizable electromagnets to generate a magnetic field have at least approximately a selected orientation and field strength, and at least one medical imaging screen and medical imaging illuminator configured to provide a medical image of the treatment region in a patient supported by the bed.

3. The apparatus of claim 2 wherein the bed is moveable and servo-controlled.

4. The apparatus according to claim 1 wherein a magnetic field provides at least about 0.1 Telsa.

5. The apparatus of claim 2 wherein the processor is configured to provide gradual, wavelike changes in the subsets of energized electromagnets and in currents flowing in the subsets of energized electromagnets.

6. The apparatus of claim 5 wherein the bed is moveable in at least a longitudinal direction.

7. The apparatus of claim 5 wherein the bed is moveable in at least a transverse direction.

8. The apparatus of claim 5 wherein the plurality of electromagnets are arranged in a plurality of rows of electromagnets, each row including a plurality of electromagnets.

9. The apparatus of claim 8 wherein the bed has an upper surface for supporting a patient, and the plurality of electromagnets are arranged exclusively below a plane defined by the upper surface of the bed.

10. The apparatus of claim 9 wherein the bed has an upper surface for supporting a patient, and the plurality of electromagnets are arranged both above and below a plane defined by the upper surface of the bed.

11. The apparatus of claim 2 further comprising an elongate, arcuate member and a servo-system configured to rotate the elongate, arcuate member, and wherein the electromagnets are mounted in a single row on the elongate, arcuate member.

12. The apparatus of claim 11, wherein the elongate, arcuate member is configured to be moveable to adjust the orientation of magnetic fields produced by the electromagnets in the treatment region when the electromagnets are energized.

13. The apparatus of claim 12, wherein the bed is moveable and servo-controlled.

14. The apparatus of claim 13 wherein the movement of the elongate, arcuate member is also servo-controlled.

15. A method for guiding an implant through a treatment region in a body comprising the steps of:
    (a) placing a body on a servo-controlled, moveable bed;
    (b) inserting a magnetically-guided treatment implant into the treatment region;
    (c) arranging a plurality of electromagnets around the treatment region so that a selected orientation of a magnetic field at a location of the treatment implant can be approximated by selectively energizing a subset of the electromagnets, moving the bed, or both; and
    (d) applying current to a selected subset of the plurality of electromagnets to provide a magnetic field at least approximating a selected magnitude and orientation at the location of the magnetically guided treatment implant sufficient to orient the magnetically-guided treatment implant in a selected orientation.

16. The method of claim 15 and further comprising:
    directing a medical imaging illuminator through a gap in the arrangement of the plurality of electromagnets at said medical imaging screen; and
    displaying a medical image of the treatment area on the medical imaging screen during the current applying step.

17. The method of claim 16 and further comprising operating the servo-controlled bed during the current applying step.

18. The method of claim 17 and further comprising applying continuously varying currents supplied to the subset of electromagnets and the subset of electromagnets to which currents are applied to provide a continuously varying magnetic field to the magnetically-guided treatment implant.

* * * * *